US012678346B2

(12) United States Patent
Yoon et al.

(10) Patent No.: US 12,678,346 B2
(45) Date of Patent: Jul. 14, 2026

(54) SUPER ABSORBENT POLYMER FILM AND ABSORBENT ARTICLE COMPRISING THE SAME

(71) Applicant: LG Chem, Ltd., Seoul (KR)

(72) Inventors: Kiyoul Yoon, Daejeon (KR); Myoungjin Shin, Daejeon (KR); Seongkyun Kang, Daejeon (KR); Yu Jin Kim, Daejeon (KR); Gicheul Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 673 days.

(21) Appl. No.: 18/010,064

(22) PCT Filed: Mar. 21, 2022

(86) PCT No.: PCT/KR2022/003866
§ 371 (c)(1),
(2) Date: Dec. 13, 2022

(87) PCT Pub. No.: WO2022/203296
PCT Pub. Date: Sep. 29, 2022

(65) Prior Publication Data
US 2023/0225916 A1 Jul. 20, 2023

(30) Foreign Application Priority Data

Mar. 26, 2021 (KR) ........................ 10-2021-0039666
Mar. 18, 2022 (KR) ........................ 10-2022-0034232

(51) Int. Cl.
*A61F 13/15* (2006.01)
*A61F 13/514* (2006.01)
(Continued)

(52) U.S. Cl.
CPC .. *A61F 13/51478* (2013.01); *A61F 13/51476* (2013.01); *A61F 2013/15373* (2013.01);
(Continued)

(58) Field of Classification Search
CPC ........ A61F 13/514; A61F 13/49; A61F 13/05; A61F 13/51401; A61F 13/51478;
(Continued)

(56) References Cited

U.S. PATENT DOCUMENTS 4,604,313 A * 8/1986 McFarland .............. D04H 1/56
428/326
5,562,645 A * 10/1996 Tanzer ................ A61F 13/5323
604/378
(Continued)

FOREIGN PATENT DOCUMENTS

CA 2057685 A1 7/1992
CN 1308654 A 8/2001
(Continued)

OTHER PUBLICATIONS

Schwalm, R. "UV Coatings Basics, Recent Developments and New Applications" Elsevier Science, Dec. 2006, p. 115, ISBN-13: 978-0444529794.
(Continued)

*Primary Examiner* — Jacqueline F Stephens
(74) *Attorney, Agent, or Firm* — Lerner David LLP

(57) ABSTRACT

The present disclosure relates to a super absorbent polymer film having excellent moisture absorption and to an absorbent article excellent in feeling capable of reducing skin rashes and other irritations generated when warmed by the wearer's body by including the super absorbent polymer film to improve external dampness. The absorbent article includes the super absorbent polymer film in addition to the absorbent material, so that dampness from the outside is remarkably reduced.

9 Claims, 2 Drawing Sheets

(51) Int. Cl.
*A61F 13/53* (2006.01)
*A61F 13/534* (2006.01)

(52) U.S. Cl.
CPC .............. *A61F 2013/15406* (2013.01); *A61F 2013/15463* (2013.01); *A61F 2013/15552* (2013.01); *A61F 2013/51409* (2013.01); *A61F 2013/530007* (2013.01); *A61F 2013/530489* (2013.01); *A61F 2013/53445* (2013.01)

(58) Field of Classification Search
CPC ......... A61F 13/51409; A61F 13/51476; A61F 13/15203; A61F 13/51462; A61F 2013/15373; A61F 2013/15463; A61F 2013/15552; A61F 2013/51409; A61F 2013/53445; A61F 2013/530489; A61L 15/16; A61L 15/22; A61L 15/42
See application file for complete search history.

(56) References Cited

U.S. PATENT DOCUMENTS

| | | | |
|---|---|---|---|
| 5,637,105 | A | 6/1997 | Tanaka et al. |
| 6,071,450 | A * | 6/2000 | Topolkaraev ........... B32B 25/08 |
| | | | 264/173.14 |
| 6,534,572 | B1 | 3/2003 | Ahmed et al. |
| 7,081,560 | B1 | 7/2006 | Lim et al. |
| 2003/0065298 | A1 | 4/2003 | Krishnaswamy-Mirle et al. |
| 2003/0134552 | A1 | 7/2003 | Mehawej et al. |
| 2004/0116287 | A1 | 6/2004 | Wang et al. |
| 2005/0049566 | A1 * | 3/2005 | Vukos ..................... A61F 13/53 |
| | | | 604/378 |
| 2006/0058769 | A1 | 3/2006 | Suzuki et al. |
| 2010/0069864 | A1 * | 3/2010 | Berland ................ D06M 23/10 |
| | | | 427/2.31 |
| 2012/0053545 | A1 | 3/2012 | Love et al. |
| 2016/0325007 | A1 | 11/2016 | Chen et al. |
| 2016/0354506 | A1 | 12/2016 | Chmielewski et al. |
| 2016/0367717 | A1 | 12/2016 | Hinayama et al. |
| 2017/0258643 | A1 | 9/2017 | Xu et al. |
| 2019/0099739 | A1 * | 4/2019 | Lee .......................... C08F 20/06 |
| 2019/0308171 | A1 | 10/2019 | Kim et al. |
| 2020/0023625 | A1 | 1/2020 | Torii et al. |
| 2020/0384441 | A1 | 12/2020 | Yoon et al. |
| 2024/0082819 | A1 | 3/2024 | Yoon et al. |

FOREIGN PATENT DOCUMENTS

| | | | |
|---|---|---|---|
| CN | 1615338 | A | 5/2005 |
| CN | 105408365 | A | 3/2016 |
| CN | 105939849 | A | 9/2016 |
| CN | 109312082 | A | 2/2019 |
| CN | 111465636 | A | 7/2020 |
| EP | 0897705 | A1 | 2/1999 |
| EP | 4074763 | A1 | 10/2022 |
| JP | H04236203 | A | 8/1992 |
| JP | H07132126 | A | 5/1995 |
| JP | 2004001461 | A | 1/2004 |
| JP | 2007275331 | A | 10/2007 |
| JP | 4148669 | B2 | 9/2008 |
| JP | 2015058034 | A | 3/2015 |
| JP | 2020000462 | A | 1/2020 |
| JP | 6716709 | B2 | 7/2020 |
| JP | 6803964 | B2 | 12/2020 |
| KR | 20020056107 | A | 7/2002 |
| KR | 20040070245 | A | 8/2004 |
| KR | 20080032923 | A | 4/2008 |
| KR | 20150037683 | A | 4/2015 |
| KR | 101720537 | B1 | 3/2017 |
| KR | 20170142059 | A | 12/2017 |
| KR | 20190004559 | A | 1/2019 |
| KR | 101966202 | B1 | 4/2019 |
| KR | 20190071619 | A | 6/2019 |
| KR | 20200000076 | U | 1/2020 |
| KR | 20210118761 | A | 10/2021 |
| WO | 2004052257 | A1 | 6/2004 |
| WO | 2020067311 | A1 | 4/2020 |

OTHER PUBLICATIONS

Odian, G. "Principles of Polymerization" John Wiley & Sons, Inc, Dec. 1981, p. 203, ISBN: 0-471-05146-2.
International Search Report for Application No. PCT/KR2022/003866 mailed Jun. 28, 2022, pp. 1-2.
Extended European Search Report including Written Opinion for Application No. 22775998.2 dated Nov. 27, 23, pp. 1-7.

* cited by examiner

【FIG. 1】
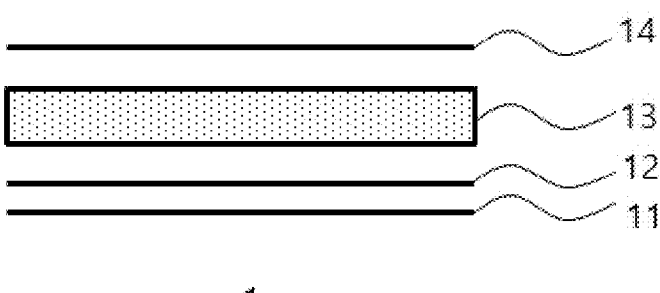
<u>1</u>
Prior Art
【FIG. 2】
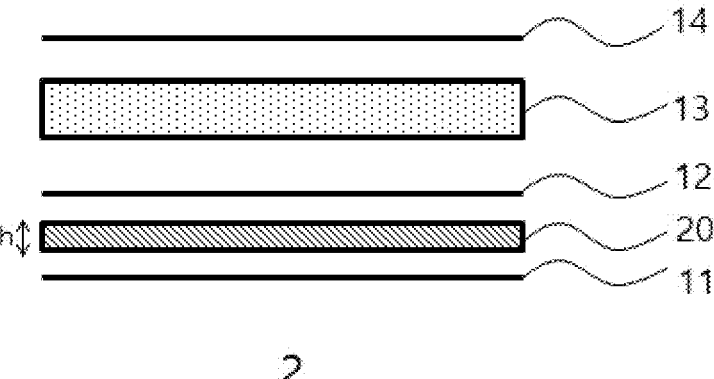
<u>2</u>
【FIG. 3】
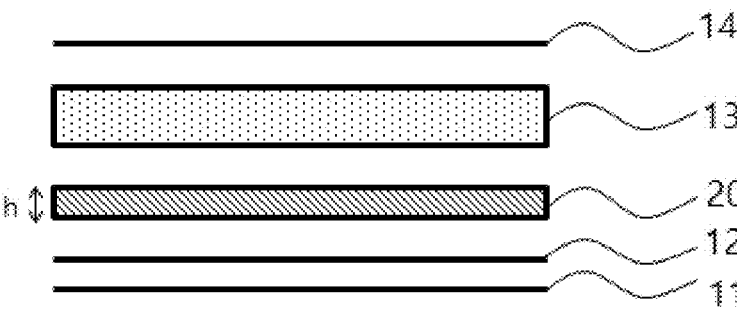
<u>3</u>

【FIG. 4】
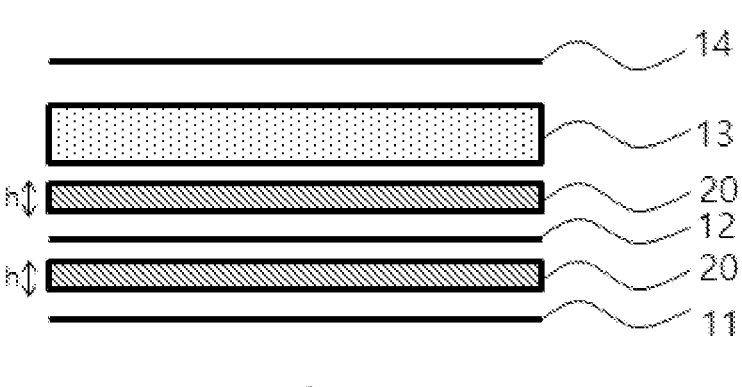
14
13
h↕     20
12
h↕     20
11
<u>4</u>

1

SUPER ABSORBENT POLYMER FILM AND ABSORBENT ARTICLE COMPRISING THE SAME

CROSS-REFERENCE TO RELATED APPLICATION(S)

This application is a national stage entry under 35 U.S.C. § 371 of International Application No. PCT/KR2022/003866 filed on Mar. 21, 2022, which claims priority from Korean Patent Applications No. 10-2021-0039666 filed on Mar. 26, 2021 and No. 10-2022-0034232 filed on Mar. 18, 2022 with the Korean Intellectual Property Office, the disclosures of which are incorporated herein by reference in their entirety.

TECHNICAL FIELD

The present disclosure relates to a super absorbent polymer film having excellent moisture absorption and to an absorbent article excellent in feeling with improved external dampness by including the super absorbent polymer film.

BACKGROUND OF ART

Absorbent articles such as disposable diapers, sanitary napkins, and incontinence pads generally include a liquid impermeable back sheet, an absorbent material, and a liquid permeable top sheet in contact with wearer's skin. If necessary, they may further include a breathable waterproof film for improving air permeability, a decorative sheet for improving the appearance, and elastic leg cuffs for improving fit and preventing side leakage.

In such absorbent articles, a material that allows body fluids to pass through the absorbent material quickly such as a synthetic polymer nonwoven fabric is used as the liquid permeable top sheet. The absorbent material is made of a super absorbent polymer, pulp, tissue, or nonwoven fabric, and functions to quickly absorb and retain the body fluids that have passed through the liquid permeable top sheet. The liquid impermeable back sheet prevents the body fluids absorbed by the absorbent material from leaking out, and a woven or nonwoven fabric made of natural or synthetic fibers is used.

The liquid impermeable back sheet is basically designed to be waterproof, but when waterproofing is too good, water vapor and air do not permeate, so there is a problem in that wearability is deteriorated. Accordingly, the liquid impermeable back sheet is usually made of a moisture permeable waterproof woven or nonwoven fabric having pores with a size that is impermeable to water particles and is permeable to smaller water vapor particles. However, due to the moisture permeability of the back sheet, moisture emitted from the absorbent material is transmitted to the outside of the back sheet. Thus, when worn for a long time, moisture is felt even outside the absorbent article, which worsens the feeling during use.

DETAILED DESCRIPTION OF THE INVENTION

Technical Problem

In order to solve the above problems, there are provided a thin super absorbent polymer film having excellent moisture absorption, and an absorbent article having improved external dampness by including the super absorbent polymer film.

Technical Solution

According to an embodiment of the present disclosure, there is provided a super absorbent polymer film having a thickness of 500 μm or less and moisture absorption of 10 to 100 g/m² measured according to KS F 2611 standard.

The super absorbent polymer film may have the thickness of 10 to 200 μm.

The super absorbent polymer film may have a moisture content of 1 to 15% and a tensile strength of 5 to 50 MPa.

According to another embodiment of the present disclosure, there is provided an absorbent article including a liquid impermeable back sheet; a breathable waterproof film; an absorbent material containing a super absorbent polymer powder and pulp; and a liquid permeable top sheet, wherein a super absorbent polymer film is included between the liquid impermeable back sheet and the breathable waterproof film and/or between the breathable waterproof film and the absorbent material, and the super absorbent polymer film has a thickness of 500 μm or less and moisture absorption of 10 to 100 g/m² measured according to KS F 2611 standard.

The super absorbent polymer film may have the thickness of 10 to 200 μm.

The super absorbent polymer film may be laminated on one side of the liquid impermeable back sheet; and/or on one side or both sides of the breathable waterproof film.

For example, the super absorbent polymer film is laminated on one side of the breathable waterproof film, and air permeability of the laminated super absorbent polymer film and breathable waterproof film may be 3000 to 5000 g/m²·24 hr.

The liquid impermeable back sheet may be a nonwoven fabric having a pore size of 20 to 1000 μm.

The breathable waterproof film may have air permeability of 2000 to 5000 g/m²·24 hr.

The absorbent material may contain 10 to 90 wt % of the super absorbent polymer powder.

The liquid permeable top sheet may have a basis weight of 15 to 30 g/m².

Advantageous Effects

The super absorbent polymer film of the present disclosure is very thin and has excellent moisture absorption, so it can be suitably used for articles requiring a moisture absorption function. In addition, the absorbent article of the present disclosure includes the super absorbent polymer film in addition to the absorbent material, so that dampness from the outside is remarkably reduced. Accordingly, it is possible to reduce skin rashes and other irritations generated when the absorbent article is warmed by the wearer's body, and the absorbent article is excellent in feeling.

BRIEF DESCRIPTION OF THE DRAWINGS

FIG. 1 is a cross-sectional view showing a configuration of a conventional absorbent article.

FIGS. 2 to 4 are cross-sectional views showing a configuration of an absorbent article according to an embodiment of the present disclosure.

DETAILED DESCRIPTION OF THE EMBODIMENTS

The terminology used herein is for the purpose of describing particular embodiments only and is not intended to be limiting of the invention. The singular forms are intended to include the plural forms as well, unless the context clearly indicates otherwise. It will be further understood that the terms "include", "have", or "possess" when used in this specification, specify the presence of stated features, steps, components, or combinations thereof, but do not preclude the presence or addition of one or more other features, steps, components, or combinations thereof.

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

Likewise, the drawings attached to the present disclosure for explaining the present invention are embodiments of the present invention, and the present invention may be embodied in various different forms, and is not limited thereto. In the drawings, parts irrelevant to the description are omitted in order to clearly explain the present invention, and like reference numerals are used for like parts throughout the disclosure. In addition, sizes and relative sizes of constituents shown in the drawings are unrelated to actual scales, and may be reduced or exaggerated for clarity of the description.

Hereinafter, the super absorbent polymer film and the absorbent article including the same of the present disclosure will be described in detail.

Super Absorbent Polymer Film

The super absorbent polymer film according to an embodiment of the present disclosure has a thickness of 500 μm or less, and moisture absorption of 10 to 100 g/m² measured according to KS F 2611 standard.

The super absorbent polymer film is an acrylic acid-based polymer in the form of a thin film that is distinct from the existing particulate super absorbent polymer. And it has a moisture content of 15% or less, is colorless and transparent, has elasticity, and exhibits excellent flexibility. The super absorbent polymer film has no risk of scattering or leaking from the absorbent article during handling, and may be used without an auxiliary agent such as pulp.

In addition, the super absorbent polymer film is thin and has excellent moisture absorption, so it can be used as a desiccant in various articles without increasing the volume or damaging the shape of the article.

Specifically, the moisture absorption of the super absorbent polymer film may be 10 g/m² or more, 13 g/m² or more, 15 g/m² or more, or 20 g/m² or more, and 100 g/m² or less, or 90 g/m² or less. The moisture absorption may be measured according to KS F 2611 standard, and a specific measurement method will be described later in Examples.

As the thickness of the super absorbent polymer film increases, the moisture absorption may increase, but when it exceeds 500 μm and is too thick, the shape of the article to be applied may be affected. Conversely, when the super absorbent polymer film is too thin, the moisture absorption effect cannot be sufficiently obtained.

In addition, when the thickness of the super absorbent polymer film exceeds 500 μm, air permeability may be reduced. However, in the case of a thin super absorbent polymer film having a thickness of 500 μm or less, flexibility of the film is greatly increased when moisture is absorbed, and capacity between polymer chains is increased, so that it is possible to exhibit moisture absorption performance while securing breathability. Therefore, it can be more suitably used for articles requiring both moisture absorption and breathability such as absorbent articles to be described later.

With this point of view, the thickness (h) of the super absorbent polymer film may preferably be 5 μm or more, 10 μm or more, or 15 μm or more, and 400 μm or less, 300 μm or less, 200 μm or less, or 150 μm or less.

Meanwhile, a moisture content of the super absorbent polymer film may be 15 wt % or less, 12 wt % or less, 11 wt % or less, or 10 wt % or less and 1 wt % or more, 2 wt % or more, 4 wt % or more, or 6 wt % or more.

The "moisture content" indicates the amount of moisture contained in the sample as a percentage with respect to the weight of the sample before drying. That is, the moisture content can be calculated by dividing a value obtained by subtracting the weight after drying of the sample from the weight before drying of the sample by the weight before drying of the sample, and then multiplying by 100. At this time, the drying condition for measuring the moisture content is that the temperature is increased to about 150° C. and maintained at 150° C., and the total drying time is 20 min including 5 min of a heating step.

The super absorbent polymer film has a thickness of 500 μm or less, and a total light transmittance with respect to visible light of 89.5% or more, indicating high transparency. The total light transmittance of the super absorbent polymer film according to an embodiment of the present disclosure may be 90% or more, 90.3% or more, 91% or more, 91.5% or more, or 92% or more. The total light transmittance may be theoretically 100%, for example, it may be 99% or less.

In addition, the super absorbent polymer film of the present disclosure may have a yellow index of 2.6 or less, 2.5 or less, 2.4 or less, 2.3 or less, 1.9 or less, 1.5 or less, or 1.3 or less, when measured in accordance with ASTM D1925 in the thickness range of 1 to 500 μm.

Meanwhile, the super absorbent polymer film may have a moisture content of 1% to 15% and a tensile strength of 5 MPa or more. Preferably, when the moisture content is 5 to 15%, the tensile strength of the super absorbent polymer film may be 10 MPa or more, 13 MPa or more, 14 MPa or more, 19 MPa or more, or 22 MPa or more, and 50 MPa or less, 47 MPa or less, 45 MPa or less, 40 MPa or less, or 35 MPa or less. The super absorbent polymer film satisfying the above tensile strength is less prone to a breakage. Thus, when it is applied to absorbent articles such as diapers, it is not easily damaged even by a wearer's movement and can exhibit excellent moisture absorption.

Meanwhile, in order to further improve the air permeability of the super absorbent polymer film, a pattern having a hole structure may be formed in the super absorbent polymer film. The shape of the pattern is not particularly limited, and a super absorbent polymer film having appropriate ventilation and moisture absorption can be manufactured by adjusting the shape, maximum diameter, average diameter, spacing between holes, and arrangement of the holes.

Alternatively, the breathability of the super absorbent polymer film may be further improved by forming a porous structure using a foaming agent such as calcium carbonate in the preparation of the super absorbent polymer film.

The above-described super absorbent polymer film may be prepared by a preparation method including the steps of: preparing a monomer composition by mixing an acrylic acid-based monomer having at least partially neutralized acidic groups, a cellulose-based thickener, a moisturizing agent, an internal cross-linking agent, a polymerization initiator, and a solvent; casting the monomer composition on a substrate to form a monomer composition film; forming a hydrogel polymer film by irradiating heat and/or light while drawing the monomer composition film; and drying the hydrogel polymer film.

According to the preparation method, a monomer composition film is prepared from a monomer composition solution having a controlled viscosity by a solution casting method, and the film is polymerized and dried to prepare a super absorbent polymer in the form of a film. In particular, the tensile strength of the super absorbent polymer film to be prepared can be adjusted by applying tension to the monomer composition film in the polymerization step, followed by drawing.

Hereinafter, the preparation method of the super absorbent polymer film will be described in detail.

The monomer composition includes an acrylic acid-based monomer having at least partially neutralized acidic groups, a cellulose-based thickener, a moisturizing agent, a polymerization initiator, and a solvent.

First, the acrylic acid-based monomer is a compound represented by the following Chemical Formula 1:

$$R^1—COOM^1 \qquad \text{[Chemical Formula 1]}$$

in Chemical Formula 1, $R^1$ is a C2 to C5 alkyl group having an unsaturated bond, and $M^1$ is a hydrogen atom, a monovalent or divalent metal, an ammonium group, or an organic amine salt.

Preferably, the acrylic acid-based monomer contains at least one selected from the group consisting of acrylic acid, methacrylic acid, and a monovalent metal salt, a divalent metal salt, an ammonium salt, and an organic amine salt thereof.

Herein, the acrylic acid-based monomers may be those having acidic groups which are at least partially neutralized. Preferably, the acrylic acid-based monomer partially neutralized with an alkali substance such as sodium hydroxide, potassium hydroxide, ammonium hydroxide, or the like may be used. A degree of neutralization of the acrylic acid-based monomer may be 40 to 95 mol %, 40 to 80 mol %, or 45 to 75 mol %. The range of the degree of neutralization can be adjusted according to final properties. An excessively high degree of neutralization causes the neutralized monomers to be precipitated, and thus polymerization may not readily occur, whereas an excessively low degree of neutralization may deteriorate the absorbency of the polymer.

In a preferred embodiment, sodium hydroxide (NaOH), potassium hydroxide (KOH), or a combination thereof may be used as the alkali substance. In particular, when potassium hydroxide is used as the alkali substance, a super absorbent polymer film having better flexibility and dimensional stability can be prepared.

The concentration of the acrylic acid-based monomer may be about 20 to about 60 wt %, preferably about 40 to about 50 wt %, based on the monomer composition including the raw materials of the super absorbent polymer and the solvent, and it may be appropriately selected in consideration of the reaction time and the reaction conditions. However, when the concentration of the monomer is excessively low, the yield of the super absorbent polymer is low and there may be a problem in economic efficiency. In contrast, when the concentration is excessively high, a problem may occur in the process such as some of the monomer is precipitated, and thus physical properties of the super absorbent polymer may be deteriorated.

Meanwhile, in the present disclosure, a thickener and a moisturizing agent are contained in the monomer composition so that the monomer composition can be applied in the form of a film by a solution casting method.

As the thickener and the moisturizing agent are contained at the same time, the monomer composition of the present disclosure may exhibit a viscosity suitable for casting in the form of a film, can maintain an appropriate moisture content in the polymerization process after film casting, and the super absorbent polymer film to be prepared may have high flexibility.

In the present disclosure, a cellulose-based thickener is used as the thickener, and specifically, at least one selected from the group consisting of nanocellulose, hydroxyethylcellulose, hydroxypropylcellulose, hydroxyethylmethylcellulose, and hydroxypropylmethylcellulose may be used. Preferably, nanocellulose, hydroxyethylcellulose, or a combination thereof may be used.

The cellulose-based thickener may be contained in an amount of 0.01 parts by weight or more, 0.1 parts by weight or more, 0.2 parts by weight or more, or 0.35 parts by weight or more, and 5 parts by weight or less, 3 parts by weight or less, 1 parts by weight or less or 0.9 parts by weight or less based on 100 parts by weight of the solid content in the monomer composition.

Herein, the solid content in the monomer composition means all components of the composition excluding the solvent. That is, the solid content means the total content of an acrylic acid-based monomer, an alkali substance for neutralizing the acrylic acid-based monomer, a cellulose-based thickener, a moisturizing agent, a cross-linking agent, a thermal initiator, a photoinitiator, an internal cross-linking agent, and other additives.

If the content of the cellulose-based thickener is less than 0.01 parts by weight based on 100 parts by weight of the solid content in the monomer composition, sufficient thickening effect cannot be ensured, so it may be difficult to prepare a monomer composition film. Conversely, if it exceeds 5 parts by weight, the viscosity of the monomer composition becomes excessively high, so that the thickness of the film becomes thick, and it may be difficult to uniformly control the thickness of the film.

As the moisturizing agent, a substance normally used as a moisturizing component in pharmaceuticals, cosmetics, chemical products, and the like may be used without limitation. Examples of the moisturizing agent include at least one selected from the group consisting of polyhydric alcohols having two or more hydroxyl groups in a molecule, citric acid, and citrate.

Specifically, as the polyhydric alcohol, a C3 to C30 polyhydric alcohol having 3 to 12 hydroxyl groups in a molecule may be used. For example, the polyhydric alcohol may be at least one selected from the group consisting of glycerin; diglycerin; propylene glycol; butylene glycol; sorbitol; polyethylene glycol; polyglycerin-3; polyglycerin-6; polyglycerin-10; and polyglyceryl-10 distearate and its derivatives (C3 to C18). Among them, at least one selected from the group consisting of glycerin, diglycerin, ethylene glycol, and sorbitol may be preferably used.

In addition, citric acid and/or citrate may also be used as the moisturizing agent. Examples of the citrate include triethylcitrate, methylcitrate, sodium citrate, trisodium 2-methylcitrate, and the like.

The moisturizing agent may be used in an amount of 5 parts by weight or more, 10 parts by weight or more, 20 parts by weight or more, or 30 parts by weight or more, and 70 parts by weight or less, 60 parts by weight or less, or 50 parts by weight or less based on 100 parts by weight of the acrylic acid-based monomer.

If the content of the moisturizing agent is less than 5 parts by weight based on 100 parts by weight of the acrylic acid-based monomer, the moisture content of the monomer composition film is not sufficient, so that the film may dry out or crumble in the subsequent polymerization and drying process and flexibility of the super absorbent polymer film to be prepared cannot be achieved. Conversely, if the content of the moisturizing agent exceeds 70 parts by weight based on 100 parts by weight of the acrylic acid-based monomer, there may be a problem in that absorbency of the super absorbent polymer film is reduced. Therefore, the content of the moisturizing agent preferably satisfies the above range.

The monomer composition contains an internal cross-linking agent for cross-linking the polymer. As the internal cross-linking agent, those used in the manufacture of existing super absorbent polymers may be used. The internal cross-linking agent may be a cross-linking agent having one or more ethylene-based unsaturated groups in addition to one or more functional groups which may react with a water-soluble substituent of the acrylic acid-based monomer; or a cross-linking agent having two or more functional groups which may react with a water-soluble substituent of the monomer and/or a water-soluble substituent formed by hydrolysis of the monomer.

As the specific example of the internal cross-linking agent, a C8-C12 bisacrylamide, bismethacrylamide, a poly(meth)acrylate of C2-C10 polyol, a poly(meth)allylether of C2-C10 polyol, or the like may be used. More specifically, at least one selected from the group consisting of N,N'-methylenebis(meth)acrylate, ethyleneoxy(meth)acrylate, polyethyleneoxy(meth)acrylate, propyleneoxy(meth)acrylate, glycerin diaciylate, glycerin triacrylate, trimethylol triacrylate, polyethylene glycol diacrylate, triallylamine, triaryl cyanurate, triallyl isocyanate, polyethylene glycol, diethylene glycol and propylene glycol may be used. In one embodiment, polyethylene glycol diacrylate may be used as the internal cross-linking agent.

The internal cross-linking agent may be contained at a concentration of 5000 ppm or less with respect to the monomer composition, so that the polymerized polymer can be cross-linked. In one embodiment, the internal cross-linking agent may be contained at 100 ppm or more, 250 ppm or more, or 500 ppm or more, and 5000 ppm or less, 4500 ppm or less, or 4000 ppm or less. The internal cross-linking agent may be adjusted to an appropriate content depending on the thickness of the super absorbent polymer film and the range of the desired tensile strength.

The polymerization initiator used in the preparation method of the super absorbent polymer film is not particularly limited as long as it is generally used for the preparation of a super absorbent polymer.

Specifically, the polymerization initiator may be an initiator for thermal polymerization or an initiator for photopolymerization by UV radiation according to the polymerization method. However, even when the photopolymerization method is applied thereto, a certain amount of heat is generated by UV radiation and the like, and some heat occurs as the polymerization reaction, an exothermal reaction, progresses. Therefore, the composition may additionally include the thermal polymerization initiator. In a preferred embodiment, a photopolymerization initiator and a thermal polymerization initiator may be used simultaneously as the polymerization initiator.

Herein, any compound which can form a radical by light such as UV rays may be used as the photopolymerization initiator without limitation.

For example, the photopolymerization initiator may be one or more compounds selected from the group consisting of benzoin ether, dialkyl acetophenone, hydroxyl alkylketone, phenyl glyoxylate, benzyl dimethyl ketal, acyl phosphine, and $\alpha$-aminoketone. Further, as the specific example of acyl phosphine, commercial lucirin TPO (2,4,6-Trimethylbenzoyldiphenylphosphine oxide), Irgacure 819 (Phenyl-bis(2,4,6-trimethylbenzoyl)phosphine oxide), and the like may be used. More various photopolymerization initiators are well disclosed in "UV Coatings: Basics, Recent Developments and New Application (Elsevier, 2007)" written by Reinhold Schwalm, p 115, and the present disclosure is not limited thereto.

A concentration of the photopolymerization initiator in the monomer composition may be 10 ppm or more, 20 ppm or more, or 40 ppm or more, and 2000 ppm or less, 1000 ppm or less, 500 ppm or less, or 100 ppm or less. If the concentration of the photopolymerization initiator is excessively low, the polymerization rate may become slow, and if the concentration is excessively high, the molecular weight of the super absorbent polymer may become low and properties may be uneven.

Furthermore, as the thermal polymerization initiator, one or more initiators selected from the group consisting of a persulfate-based initiator, an azo-based initiator, hydrogen peroxide, and ascorbic acid may be used. Specifically, sodium persulfate ($Na_2S_2O_8$), potassium persulfate ($K_2S_2O_8$), ammonium persulfate (($NH_4$)$_2S_2O_8$), and the like may be used as examples of the persulfate-based initiators; and 2,2-azobis(2-amidinopropane) dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid), and the like may be used as examples of azo-based initiators. More various thermal polymerization initiators are well disclosed in "Principle of Polymerization (Wiley, 1981)" written by Odian, p 203, and the present disclosure is not limited thereto.

A concentration of the thermal polymerization initiator in the monomer composition may be 10 ppm or more, 100 ppm or more, or 500 ppm or more, and 2000 ppm or less, 1500 ppm or less, or 1000 ppm or less. If the concentration of the thermal polymerization initiator is excessively low, additional thermal polymerization hardly occurs and the effect of adding the thermal polymerization initiator may be insufficient. If the concentration of the thermal polymerization initiator is excessively high, the molecular weight of the super absorbent polymer may become low and the properties may be uneven.

The monomer composition may further contain an additive such as a plasticizer, a preservation stabilizer, and an antioxidant, if necessary.

Alternatively, the monomer composition may further contain a foaming agent as an additive. The super absorbent polymer film prepared from such a monomer composition has a porous structure having a plurality of pores, thereby exhibiting higher air permeability.

The foaming agent may be foamed during polymerization and/or drying, and may be, for example, at least one selected from the group consisting of expandable microsphere, expanded microsphere, an azo compound, and an inorganic foaming agent. These foaming agents form a large number of pores in the super absorbent polymer film, and thus the initial absorbency of the super absorbent polymer film can be greatly improved.

The expandable microsphere may have a structure having a core containing hydrocarbon, and a shell surrounding the core and containing a thermoplastic resin.

The hydrocarbon constituting the core of the expandable microsphere may be at least one selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane and cyclooctane. Among them, a C3 to C5 hydrocarbon (n-propane, n-butane, iso-butane, cyclobutane, n-pentane, iso-pentane, cyclopentane) may be suitable.

In addition, the thermoplastic resin constituting the shell of the expandable microsphere may be a polymer formed from at least one monomer selected from the group consisting of (meth)acrylate, (meth)acrylonitrile, aromatic vinyl, vinyl acetate, vinyl halide and vinylidene halide. Among them, a copolymer of (meth)acrylate and (meth)acrylonitrile, or a (meth)acrylate homopolymer is most suitable for achieving the initial absorbency within the above-described range.

The expandable microsphere is a foaming agent which expands by supplying heat, and may expand under high-temperature conditions in the polymerization and/or drying step of monomers to form pores in the super absorbent polymer film. This expandable microsphere may have expansion properties which may vary depending on components constituting the core and the shell, weights of the respective components, and particle sizes thereof. By adjusting these factors, it is possible to expand pores to a desired size and to control a pore structure of the super absorbent polymer film.

The expandable microspher may have an average particle diameter (D50) before expansion of 2 μm or more, 5 μm or more, 7 μm or more, or 10 μm or more, and 50 μm or less, 40 μm or less, or 35 μm or less. When the expandable microspher has the average particle diameter as described above, it can be determined as suitable for achieving appropriate porosity.

At this time, the average particle diameter (D50) of the expandable microsphere may be measured by dispersing the powder to be measured in dispersion medium, introducing the powder into a commercially available laser diffraction particle size analyzer (e.g., Mastersizer 3000), and then measuring a difference of diffraction pattern according to the particle size when the particles pass through the laser beam, followed by calculating a particle size distribution.

Whether the expandable microsphere can form pores with an appropriate size in the super absorbent polymer film can be confirmed by confirming the expansion ratio and size after foaming the capsule in air.

The super absorbent polymer film prepared according to the present disclosure has a thickness of 0.8 mm or less, preferably 0.001 to 0.8 mm, and the pore size is suitably about 10 to 500 μm. Accordingly, in order to form pores with an appropriate size in the super absorbent polymer film, it is necessary to understand expansion properties of expandable microsphere.

Specifically, the expandable microsphere is applied on a glass petri dish, which is then heated in air for 10 minutes to expand the expandable microsphere. In this regard, when the expandable microsphere exhibits a maximum expansion ratio of 3 times to 15 times, 2 times to 12 times, or 1 time to 7 times in air, it is suitable for preparing a super absorbent polymer film having pores with an appropriate size.

Further, when the expandable microsphere exhibits a maximum expansion size of 150 μm or less in air, pores with an appropriate size may be formed. Specifically, when the expandable microsphere exhibits a maximum expansion size of 10 to 500 μm, 50 to 300 μm, 70 to 150 μm, or 75 to 150 μm in air, it is suitable for preparing a super absorbent polymer film having pores with an appropriate size.

In the expandable microsphere, expansion may begin at 60 to 200 C, 70 to 170° C., or 80 to 165° C., and maximum expansion may be reached at 100 to 240° C., 120 to 200° C., or 130 to 190° C.

Examples of the expandable microsphere include Expancel DU series from Nouryon such as Expancel 461 DU 40, Expancel 461 DU 20, Expancel 031 DU 40, Expancel 053 DU 40, and Expancel 551 DU 40; and/or Microsphere F series from Matsunomo such as Microsphere F-AC170D, Microsphere F-36, Microsphere F-36LV, Microsphere F-48, Microsphere F-80GS, and Microsphere F-50. Preferably, Expancel 031 DU 40 having a core containing hydrocarbon and a shell containing a copolymer of acrylate and acrylonitrile and/or Microsphere F-AC170D having a core containing hydrocarbon and a shell containing an acrylate copolymer can be used, but the present disclosure is not limited thereto.

The expanded microsphere is a foaming agent in an expanded state before use, and may be one in which an inorganic material such as talc and/or calcium carbonate is coated on the surface of hollow thermoplastic resin particles.

The thermoplastic resin may be a polymer formed from at least one monomer selected from the group consisting of (meth)acrylate, (meth)acrylonitrile, aromatic vinyl, vinyl acetate, vinyl halide, and vinylidene halide.

Preferably, the expanded microsphere may be one in which calcium carbonate is coated on the surface of hollow particles of (meth)acrylate and/or (meth)acrylonitrile copolymer.

The hollow thermoplastic resin particles of the expanded microsphere no longer expand, but shrink upon heating. However, the inorganic material on the surface exhibits foamability. Accordingly, pores having a size similar to that of the expanded microsphere can be formed, and thus the size of pores formed in the super absorbent polymer film can be adjusted by appropriately selecting the particle size of the expanded microsphere.

Thus, when the expanded microsphere has an average particle diameter (D50) of 10 μm or more, 20 μm or more, or 30 μm or more, and 150 μm or less, 130 μm or less, or 120 μm or less, it is suitable for preparing a super absorbent polymer film having pores with an appropriate size. Herein, the average particle diameter may be measured using the same method as in the expandable microsphere.

Meanwhile, the foaming temperature of the expanded microsphere may be 130° C. or more, 140° C. or more, or 150° C. or more, and 200° C. or less, or 180° C. or more.

Examples of the expanded capsule include Microsphere MFL series from Matsunomo such as MFL-110CAL, MFL-100MCA, MFA HD60CA, MFL HD30CA, and MFL-SEVEN. Preferably, MFL-110CAL in which calcium carbonate powder is coated on the surface of hollow particles of a copolymer of acrylate and acrylonitrile may be used, but the present disclosure is not limited thereto.

s the azo-based compound, an azoamidine-based compound such as 2,2'-azobis(2-methylpropionamidine)dihydrochloride and 2,2-azobis[N-(2-carboxyethyl)-2-methylpropionamidine]tetrahydrate may be used, and preferably, 2,2'-azobis(2-methylpropionamidine)dihydrochloride may be used.

As the inorganic foaming agent, at least one selected from the group consisting of calcium carbonate ($CaCO_3$), sodium bicarbonate ($NaHCO_3$), ammonium bicarbonate ($NH_4HCO_3$), ammonium carbonate (($NH_4$)$_2CO_3$), ammonium nitrite ($NH_4NO_2$), sodium borohydride ($NaBH_4$), and sodium carbonate ($Na_2CO_3$) may be used, and, preferably, calcium carbonate may be used.

As the inorganic foaming agent, micro- or nano-sized particles having a particle diameter of 1 nm to 100 μm may be used, and an appropriate type may be selected according to desired physical properties of the super absorbent polymer sheet. Herein, the particle size of the inorganic foaming agent may be measured by the above-described laser diffraction method, or may be measured by a scanning electron microscope (SEM).

In the present disclosure, the expandable microsphere, expanded microsphere, azo-based compound, and inorganic foaming agent may each be used as the foaming agent, or at least one foaming agent may be used in combination therewith.

Meanwhile, when at least one of the expandable microsphere and the expanded microsphere is used as a first foaming agent and at least one of the azo-based compound and the inorganic foaming agent is used as a second foaming agent, a weight ratio of the first foaming agent and the second foaming agent may be 1:0.3 to 1:3, or 1:0.5 to 1:2. When satisfying the weight ratio, an improved initial absorption rate may be exhibited as described above.

Meanwhile, the foaming agent may be contained in an amount of 0.1 to 10 parts by weight, more preferably 0.5 to 7 parts by weight, or 1 to 5 parts by weight based on 100 parts by weight of the monomer composition.

If the foaming agent is contained in an amount of less than 0.1 parts by weight based on 100 parts by weight of the monomer composition, a porous structure of the super absorbent polymer film by foaming cannot be secured, and thus the effect of improving the initial absorption rate cannot be obtained.

In addition, when the foaming agent is contained in excess of 10 parts by weight based on 100 parts by weight of the monomer composition, there may be a problem in that the degree of cross-linking of the polymer is lowered due to the foaming agent during polymerization. In addition, since the expandable microsphere foaming agent and the expanded microsphere foaming agent have low solubility in a solvent (e.g., water) and low density, if the content exceeds 10 parts by weight based on 100 parts by weight of the monomer composition, a phenomenon in which the foaming agent is precipitated from the monomer composition may occur, and thus foaming may not be performed well.

Most of the above foaming agents are actively foamed at 80° C. or more, or 100° C. or more. Accordingly, the foaming of the foaming agent may mainly occur in the drying step of the hydrogel polymer film.

The raw materials such as the acrylic acid-based unsaturated monomer, the cellulose-based thickener, the moisturizing agent, the internal cross-linking agent, the polymerization initiator, and the additive may be prepared in the form of a monomer composition solution dissolved in a solvent.

Any solvent which can dissolve the components may be used without limitation, and for example, one or more solvents selected from water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butyrolactone, carbitol, methylcellosolve acetate, N,N-dimethylacetamide, and the like may be used alone or in combination. For example, water may be used as the solvent.

In the present disclosure, the monomer composition exhibits a viscosity suitable for a solution casting method by containing a cellulose-based thickener and a moisturizing agent. Specifically, the viscosity at 25° C. of the monomer composition may be 100 mPa·s or more, 140 mPa·s or more, or 200 mPa·s or more, and 5000 mPa·s or less, 2300 mPa·s or less, 2000 mPa·s or less, 1500 mPa·s or less, or 1400 mPa·s or less. The viscosity of the monomer composition may be measured with a viscometer (e.g., TV-22 manufactured by TOKI) under the conditions of spindle #1 and a rotation speed of 1 rpm.

If the viscosity of the monomer composition is less than 100 mPa·s, it may be difficult to cast the monomer composition film to a uniform thickness, and polymerize it while drawing it. Conversely, if the viscosity of the monomer composition exceeds 5000 mPa·s, it is difficult to prepare a uniform monomer composition, and flowability of the monomer composition is low, so that processability is deteriorated and defoaming is difficult.

The monomer composition is prepared, and then casted on a substrate to prepare a monomer composition film. Then, it is polymerized while drawing it to form a hydrogel polymer film. Casting and polymerization of the monomer composition may be continuously performed through a roll-to-roll process.

First, the monomer composition is applied on a substrate to prepare a monomer composition film.

Specifically, a polyethylene terephthalate (PET) film in which at least one surface is hydrophobically treated with silicone or fluorine, which is usually used as a release film, may be used as the substrate. For example, the substrate may be a PET film surface-treated with a siloxane-based polymer or polytetrafluoroethylene (Teflon®). However, the material of the substrate is not limited thereto, and a suitable substrate may be selected depending on the composition and properties of the monomer composition.

For example, the PET film in which its surface is hydrophobically treated may have a water contact angle of 105° to 110°, and a surface energy of 20 to 25 mN/m. Such hydrophobic-treated PET film not only facilitates application of the monomer composition film, but also facilitates peeling of the hydrogel polymer film to be prepared after polymerization, thereby improving the convenience of the manufacturing process. In particular, when the above-described polyether-modified siloxane-based surfactant is contained in the monomer composition, an affinity with the hydrophobic-treated PET film having the above contact angle and surface energy is high, so that casting with a uniform thickness is possible. Thus, a uniform and thin film can be formed even in a roll-to-roll continuous process, thereby further improving productivity.

Unlike the general polymer solution casting method in which the solvent is removed after casting the polymer solution, the present disclosure immediately performs the drawing and polymerization process after the monomer composition is applied on the substrate so as not to decrease the moisture content.

If the moisture content of the monomer composition film is too low, components constituting the monomer composition may be precipitated before polymerization, and there may be a problem in that the film is broken after polymerization. Accordingly, the moisture content of the monomer composition film preferably satisfies the range of 30 wt % to 60 wt %, 30 wt % to 50 wt %, or 30 wt % to 45 wt %.

The thickness of the monomer composition film may be appropriately adjusted depending on the thickness of the desired super absorbent polymer film. Although the thickness of the monomer composition film hardly changes during the polymerization step, the thickness may decrease by about 10 to 40% or 15 to 35% while the moisture content decreases during the drying process of the hydrogel polymer film after polymerization. In consideration of this, a monomer composition film may be prepared with an appropriate thickness.

For example, the thickness of the monomer composition film may be 800 μm or less, 600 μm or less, or 500 μm or less, and 1 μm or more, 5 μm or more, or 10 μm or more, but is not limited thereto. It can be appropriately adjusted depending on the composition of the monomer composition, specific conditions in the polymerization and drying steps, and the thickness of the desired super absorbent polymer film.

Subsequently, a polymerization reaction is performed by irradiating heat and/or light while drawing the monomer composition film in the longitudinal direction (MD direction) to form a hydrogel polymer film. Drawing the film during polymerization as described above can control physical properties such as tensile strength of the super absorbent polymer film to be prepared.

At this time, the tension applied to the monomer composition film may be 40 N/m or more, 45 N/m or more, 50 N/m or more, or 60 N/m or more, and 100 N/m or less, 90 N/m or less, or 70 N/m or less. If the film is drawn by applying an excessively large tension, the monomer composition film may be broken or the thickness may be excessively thin, and if the tension is too small, physical properties such as tensile strength of the film may not be achieved.

The polymerization temperature may be appropriately adjusted depending on the composition of the monomer composition, but is preferably 40° C. or more, or 50° C. or more for the smooth reaction. In addition, if the temperature is too high, the solvent evaporates and components constituting the monomer composition may be precipitated. Therefore, the polymerization temperature is preferably 90° C. or less or 80° C. or less.

The moisture content of the hydrogel polymer film prepared through the polymerization step may be about 20 wt % or more, preferably 25 wt % or more, and 40 wt % or less, or 35 wt % or less. Accordingly, the hydrogel polymer film is dried to prepare a final super absorbent polymer film.

The temperature of the drying step may be preferably 80 to 150° C., or 90° C. to 100° C. Drying for about 5 to 30 minutes within the above temperature range may provide a super absorbent polymer film having the moisture content of 15 wt % or less, 12 wt % or less, 10 wt % or less, or 9 wt % or less, and 1 wt % or more, 2 wt % or more, 4 wt % or more, or 6 wt % or more.

Absorbent Article

The absorbent article according to an embodiment of the present disclosure is characterized by including the above-described super absorbent polymer film between a liquid impermeable back sheet and an absorbent material. Accordingly, the absorbent article may be excellent in feeling by improving external dampness by the moisture emitted from the absorbent material absorbing the liquid.

FIG. 1 is a cross-sectional view showing a configuration of a conventional absorbent article 1. The conventional absorbent article 1 includes a liquid impermeable back sheet

11, a breathable waterproof film 12, an absorbent material 13, and a liquid permeable top sheet 14.

In contrast, as shown in FIGS. 2 to 4, the absorbent articles 2, 3, 4 of the present disclosure includes a super absorbent polymer film 20 between a liquid impermeable back sheet 11 and a breathable waterproof film 12, and/or between a breathable waterproof film 12 and an absorbent material 13. The super absorbent polymer film has a thickness (h) of 500 μm or less, and has moisture absorption of 10 to 100 g/m² measured according to KS F 2611 standard, thereby absorbing moisture emitted from the absorbent material to the outside to keep the feeling during use dry.

When the super absorbent polymer film is interposed both between the liquid impermeable back sheet 11 and the breathable waterproof film 12 and between the breathable waterproof film 12 and the absorbent material 13 as shown in FIG. 4, the thickness (h) and/or physical properties of each super absorbent polymer film may be the same or different from each other.

Hereinafter, the absorbent article of the present disclosure will be described in detail for each component.

Super Absorbent Polymer Film

In the absorbent article of the present disclosure, the above-described super absorbent polymer film is interposed between a liquid impermeable back sheet and a breathable waterproof film and/or between a breathable waterproof film and an absorbent material.

As described above, the super absorbent polymer film has excellent moisture absorption, and thus can significantly improve dampness outside the back sheet by absorbing moisture emitted from the absorbent material. In addition, since the super absorbent polymer film has a thickness of 500 μm or less, it exhibits the above-described moisture absorption performance without significantly increasing the thickness of the absorbent article, thereby remarkably improving the feeling during use of the absorbent article.

Liquid Impermeable Back Sheet

As the liquid impermeable back sheet of the absorbent article, a nonwoven fabric prepared by spinning an olefin-based resin such as polyethylene and polypropylene may be used. The preparation method of the nonwoven fabric is not particularly limited, and those prepared by processing methods such as air-laid, thermal bond, spunlace, spunbond, meltblown, and stitchbond may be used without limitation.

The nonwoven fabric used for the liquid impermeable back sheet may have a pore size of 20 to 1000 μm, 50 to 700 μm, or 10 to 300 μm. When the pores of the woven or nonwoven fabric satisfy the above range, the permeation of liquid is blocked and the permeation of water vapor and air is possible, thereby exhibiting an excellent fit.

The basis weight of the liquid impermeable back sheet is not particularly limited, but when it is about 10 to 25 g/m², preferably about 12 to 20 g/m², it is possible to further improve the feel while preventing excrement absorbed in the absorbent core from leaking to the outside.

The above-described liquid impermeable back sheet and the super absorbent polymer film may be first laminated by a method such as thermal bonding before manufacturing the absorbent article. Specifically, the super absorbent polymer film may be laminated on one side of the liquid impermeable back sheet, and the absorbent article may be manufactured by laminating a breathable waterproof film, an absorbent material, and a liquid permeable top sheet on the super absorbent polymer film of the laminate.

Breathable Waterproof Film

Meanwhile, the absorbent article of the present disclosure includes, on the liquid impermeable back sheet, a breathable waterproof film that allows air to flow more smoothly while being waterproof.

The breathable waterproof film can be prepared by blending a thermoplastic polymer with an additive to prepare a resin composition, and molding the resin composition using casting or expansion film extrusion, or other suitable film-forming technique. The resin composition may have a composition of, for example, 40 to 60% of the thermoplastic polymer and 40 to 60% of the additive. The additive may be various components depending on desired properties such as antioxidants, filler particles, dyes, and the like.

For example, a film prepared by casting a resin composition in which a thermoplastic polymer and an additive are blended is drawn uniaxially or biaxially through three steps of a preheating process, a drawing process, and a heat setting process to produce a waterproof film with breathability.

The thermoplastic polymer includes soluble polyolefins such as very low density polyethylene (VLDPE), low density polyethylene (LDPE), high density polyethylene (HDPE), polypropylene, a copolymer of ethylene and C3-C12 alpha-olefin, a copolymer of propylene and ethylene and/or C4-C12 alpha-olefin, and a propylene-based polymer containing both atactic and isotactic propylene units in the polypropylene mainchain; block copolymers such as elastomers, polyurethane, copolyether ester, a polyamide polyether block copolymer, an ethylene vinylacetate copolymer, copoly(styrene/ethylene-butylene), styrene-poly(ethylene-propylene)-styrene, styrene-poly(ethylene-butylene)-styrene, polystyrene/poly(ethylene-butylene)/polystyrene, and poly(styrene/ethylene-butylene/styrene); and the like, but the present disclosure is not limited thereto.

As the additive, a filler such as calcium carbonate ($CaCO_3$) may be used. Calcium carbonate is a white solid material produced by the reaction of carbonate ions and calcium ions, and can form a number of holes in the film while being bonded by a polymer resin. In the present disclosure, the content of calcium carbonate is controlled in the range of 40 to 45 wt % based on the total weight of the composition for forming a breathable waterproof film in the preparation of the breathable waterproof film, and the draw ratio of the film is adjusted in the range of 2.5 to 3.5 times in the mechanical direction in consideration of tensile strength and moisture permeability. Accordingly, the size of the hole formed in the film is adjusted, and thus the excrement absorbed in the absorbent material does not leak to the outside, and air or water vapor can more smoothly permeate through the back sheet.

Specifically, when the content of calcium carbonate and the draw ratio of the film are adjusted in the above-described ranges, holes having a size (diameter) of about 10 to 90 μm, preferably about 40 to 60 μm, can be formed in the film. The size of these holes is smaller than the size of water particles, which is 100 μm or more, and larger than the size of vapor, which is about 0.001 to 0.01 μm. Therefore, the excrement absorbed in the absorbent material does not leak to the outside due to the breathable waterproof film, but hot air or water vapor inside the diaper can be easily discharged to the outside through the breathable waterproof film.

The breathable waterproof film may have air permeability of 2000 to 5000 g/m²·24 hr, preferably 3500 to 4500 g/m²·24 hr. When the air permeability is within the above range, it is possible to more effectively prevent side effects on the skin caused by humid air.

The basis weight of the breathable waterproof film is not particularly limited. However, when it is about 15 to 22 g/m², strength of the film is more improved, and air permeability of the film can be adjusted in the range of about 3500 to 4500 g/m²·24 hr. Accordingly, it is possible to prevent the excrement absorbed in the absorbent core from leaking to the outside, and air or water vapor can smoothly permeate through the back sheet, thereby further improving wearer's fit.

The above-described breathable waterproof film and super absorbent polymer film may be laminated by a method such as thermal bonding before manufacturing an absorbent article. As an example, the super absorbent polymer film is laminated on one side of the breathable waterproof film, and air permeability of the laminated super absorbent polymer film and breathable waterproof film may be 3000 g/m²·24 hr or more, or 3200 g/m²·24 hr or more, and 5000 g/m²·24 hr or less, 4500 g/m²·24 hr or less, or 4200 g/m²·24 hr or less. As described above, the super absorbent polymer film exhibits excellent moisture absorption and high air permeability, so that moisture absorption performance can be imparted to the absorbent article without deterioration in breathability.

Absorbent Material

The absorbent material used in the absorbent article of the present disclosure contains a super absorbent polymer powder, which is an aggregate of super absorbent polymer particles, and pulp.

As the super absorbent polymer powder, a material generally used for imparting absorption performance to an absorbent article may be used without limitation. The super absorbent polymer may be, for example, at least one selected from the group consisting of a cross-linked product of an acrylate polymer, a cross-linked product of a vinyl alcohol-acrylate copolymer, a cross-linked product of maleic anhydride graft polyvinyl alcohol, a cross-linked product of an acrylate-methacrylate copolymer, a cross-linked product of a saponified product of a methyl acrylate-vinyl acetate copolymer, a cross-linked product of a starch-acrylate graft copolymer, a cross-linked product of a saponified product of a starch-acrylonitrile graft copolymer, a cross-linked product of carboxymethyl cellulose, a cross-linked product of an isobutylene-maleic anhydride copolymer and a cross-linked product of a methylene oxide polymer. Preferably, it may be a cross-linked product of an acrylate polymer.

The size of the super absorbent polymer particles constituting the super absorbent polymer powder may be 100 to 1,000 μm, 150 to 800 μm, or 300 to 600 μm. When the size of the super absorbent polymer particles is less than 100 μm, the super absorbent polymer gel swollen by absorbing body fluids may be discharged to the outside of the absorbent article or a gel blocking phenomenon may occur to impair physical properties. When the particle size exceeds 1,000 μm, it is difficult to slim the absorbent article.

The super absorbent polymer powder may be contained in an amount of 10 to 90 wt %, preferably 20 wt % or more, 30 wt % or more, or 40 wt % or more and 80 wt % or less, or 60 wt % or less of the total weight of the absorbent material.

The pulp used in the absorbent material may be cellulose fluff pulp formed by pulverizing wood pulp. The pulp absorbs the liquid quickly and may act to separate the super absorbent polymer particles from each other to reduce gel adhesion.

For this effect, the pulp may be contained in an amount of 10 to 90 wt %, preferably 20 wt % or more, or 40 wt % or more, and 80 wt % or less, 70 wt % or less, or 50 wt % or less of the total weight of the absorbent material.

Specifically, the super absorbent polymer may be contained in an amount of about 10 to 90 wt %, preferably about 30 to 60 wt % based on the total weight of the absorbent core, and the pulp may be contained in an amount of about 10 to 90 wt %, preferably about 40 to 70 wt % based on the total weight of the absorbent material.

The absorbent material may further contain synthetic fibers such as polyethylene fibers, polypropylene fibers, polyester fibers, polyamide fibers, rayon fibers, polyurethane fibers, and the like, in addition to the super absorbent polymer powder and the pulp, if necessary. In this case, binding force between the super absorbent polymer powder and the pulp can be further improved. These synthetic fibers may be used in an amount of 20 wt % or less, or 10 wt % or less of the total weight of the absorbent material.

The method for preparing the absorbent material is not particularly limited. For example, it can be prepared by uniformly mixing a super absorbent polymer powder, pulp, and optionally synthetic fibers, extruding the mixture for molding, and then packaging the extruded product with a packaging material such as a tissue.

Liquid Permeable Top Sheet

As the liquid permeable top sheet, a material that is soft and does not irritate the user's skin while having hydrophilicity may be suitably used so that a liquid can quickly permeate therethrough.

The liquid permeable top sheet may be, for example, a hydrophilic nonwoven fabric, an anti-blocking film such as an anti-blocking polyethylene film, or a foamed film such as urethane foam, and may be used by laminating one or more thereof.

Preferably, the liquid permeable top sheet may be a hydrophilic nonwoven fabric manufactured using synthetic fibers or natural fibers such as polypropylene, polyethylene, polyester, polyethylene terephthalate, rayon, and cotton. The preparation method of the nonwoven fabric is not particularly limited, and those prepared by processing methods such as air-laid, thermal bond, spunlace, spunbond, meltblown, and stitchbond may be used without limitation.

The fineness of the liquid permeable nonwoven fabric is not particularly limited. However, when the fineness is in the range of about 1.5 to 6 denier (d), preferably about 1.5 to 2 denier (d), skin irritation is minimized when the absorbent article is worn, thereby minimizing the occurrence of side effects on the skin and improving instantaneous absorption.

In addition, the length of the fiber is not particularly limited, but when it is about 36 to 39 mm, processability of a carding process in manufacturing the nonwoven fabric can be improved, and surface uniformity of the nonwoven fabric is improved to minimize friction on the wearer's skin.

The basis weight of the nonwoven fabric formed of these fibers is not particularly limited, but when it is about 15 to 30 g/m², preferably about 15 to 20 g/m², it is possible to improve absorption and make the surface softer, thereby minimizing side effects on the skin.

Preparation Method of Absorbent Article

The preparation method of an absorbent article is not particularly limited. The absorbent article of the present disclosure can be prepared by laminating components, that is, the liquid impermeable back sheet, the super absorbent polymer film, the breathable waterproof film, the absorbent material, and the liquid permeable top sheet, in an appropriate order and then fixing them using embossing, or fixing them using an adhesive such as a hot melt adhesive.

For example, when the super absorbent polymer film is interposed between the breathable waterproof film and the absorbent material, the absorbent article may be manufactured by laminating the liquid impermeable back sheet, the breathable waterproof film, the super absorbent polymer film, the absorbent material, and the liquid permeable top sheet in this order, and then fixing them with an adhesive or embossing.

Alternatively, the absorbent article may be manufactured by first thermally bonding the super absorbent polymer film to the liquid impermeable back sheet or the breathable waterproof film, and then laminating them with other components, followed by fixing.

Meanwhile, when the super absorbent polymer film is interposed between the liquid impermeable back sheet and the breathable waterproof film, the super absorbent polymer film is first laminated on one side of the liquid impermeable back sheet, and then the breathable film is laminated on the upper side of the super absorbent polymer film (the side not contact with the liquid impermeable back sheet). Thereafter, the absorbent material and the liquid permeable top sheet are laminated thereon, and then fixed to prepare an absorbent article.

Alternatively, the absorbent article may be manufactured by first laminating a super absorbent polymer film on one or both sides of a breathable waterproof film, placing them on a liquid impermeable back sheet, and then laminating an absorbent material and a liquid permeable top sheet, followed by fixing.

Lamination of the super absorbent polymer film and the liquid impermeable back sheet, and lamination of the super absorbent polymer film and the breathable waterproof film may be performed by thermal bonding, and the temperature and pressure of thermal bonding may be appropriately adjusted according to the properties of the liquid impermeable back sheet, the breathable waterproof film, and the super absorbent polymer film used.

The absorbent article may be a disposable diaper, a sanitary napkin, or an incontinence pad.

Hereinafter, the present invention will be described in more detail with the following preferred examples, but these examples are provided for illustrative purposes only. It is apparent to those skilled in the art that various changes and modifications can be made within the scope and spirit of the present invention. Therefore, it is obvious that the changes and modifications are within the scope of the present invention.

EXAMPLES

<Preparation of Super Absorbent Polymer Film>

Example 1-1

A neutralized solution in which 70 mol % of acrylic acid was neutralized was prepared by mixing 55 g of acrylic acid, 66.6 g of a 45 wt % potassium hydroxide (KOH) solution, and 55 g of water.

Hydroxyethyl cellulose (HEC, Natrosol 250HR manufactured by Ashland), glycerin, sodium persulfate as a thermal polymerization initiator, and Irgacure 819 as a photopolymerization initiator were added to the neutralized solution to prepare a monomer composition having a solid content (TSC) of 54 wt %.

At this time, HEC was added in an amount of 0.45 parts by weight based on 100 parts by weight of the solid content in the monomer composition, and glycerin was added in an amount of 40 parts by weight based on 100 parts by weight of acrylic acid. In addition, the thermal polymerization initiator and the photopolymerization initiator were added in an amount of 1000 ppm and 80 ppm based on the total weight of the monomer composition, respectively.

A viscosity of the prepared monomer composition at 25° C. was measured using TV-22 viscometer manufactured by TOKI under the conditions of spindle #1 and a rotation speed of 1 rpm, and the viscosity of the monomer composition was confirmed to be 201 mPa·s.

Subsequently, the monomer composition was coated on one side of a polyethylene terephthalate (PET) film to form a 20 μm thick monomer composition film (moisture content of 30%). A comma coater was used for coating, and an applicator roll moved at 0.5 m/min.

Then, polymerization was performed by irradiating UV light of 370 mJ/cm² to the monomer composition film to form a hydrogel polymer film. Herein, a polymerization reaction was performed while drawing the monomer composition film by applying a tension of 60 N/m in the MD direction. The thickness of the prepared hydrogel polymer film was 20 μm, and it was confirmed that there was no significant change compared to the monomer composition and the moisture content was 15 wt %.

Subsequently, the prepared hydrogel polymer film was dried at a temperature of 80° C. for 5 minutes to prepare a super absorbent polymer film (SAP film) having a moisture content of 10 wt % and a thickness of 17 μm.

The moisture content was calculated by the following formula with the weight before drying (a) and the weight after drying (b) of the super absorbent polymer film. At this time, the super absorbent polymer film was dried in such a way that the temperature was increased from room temperature (25° C.) to 150° C. over 5 minutes, and then maintained at 150° C. for 15 minutes.

$$\text{Moisture content } (\%)=(a-b)/a*100$$

Example 1-2

A super absorbent polymer film having a moisture content of 10 wt % and a thickness of 45 μm was prepared in the same manner as in Example 1-1, except that the thickness of the monomer composition film was 50 μm, the drying temperature of the hydrogel polymer was 80° C., and the drying time was 10 minutes.

Example 1-3

A super absorbent polymer film having a moisture content of 10 wt % and a thickness of 149 μm was prepared in the same manner as in Example 1-1, except that the thickness of the monomer composition film was 160 μm, the drying temperature of the hydrogel polymer was 90° C., and the drying time was 10 minutes.

Example 1-4

A neutralized solution in which 70 mol % of acrylic acid was neutralized was prepared by mixing 55 g of acrylic acid, 66.6 g of a 45 wt % potassium hydroxide (KOH) solution, and 55 g of water.

An internal cross-linking agent (polyethylene glycol diacrylate (PEGDA), MW=400, manufacturer: Aldrich), expanded microsphere (MFL110CAL, manufactured by Matsumoto Yushi-Seiyaku, average particle diameter: 90-120 μm, foaming temperature: 160-170° C.) as a foaming agent, hydroxyethyl cellulose (HEC, Natrosol 250HR manufactured by Ashland), glycerin, sodium persulfate as a thermal polymerization initiator, and Irgacure 819 as a photopolymerization initiator were added to the neutralized solution to prepare a monomer composition having a solid content (TSC) of 40 wt %.

At this time, the foaming agent was added in an amount of 1 parts by weight based on 100 parts by weight of the monomer composition, HEC was added in an amount of 0.45 parts by weight based on 100 parts by weight of the solid content in the monomer composition, and glycerin was added in an amount of 40 parts by weight based on 100 parts by weight of acrylic acid. In addition, the thermal polymerization initiator, and the photopolymerization initiator were added in an amount of 1000 ppm, and 80 ppm based on the total weight of the monomer composition, respectively.

A viscosity of the prepared monomer composition at 25° C. was measured using TV-22 viscometer manufactured by TOKI under the conditions of spindle #1 and a rotation speed of 1 rpm. As a result, the viscosity of the monomer composition was confirmed to be 211 mPa·s.

Subsequently, the monomer composition was coated on one side of a polyethylene terephthalate (PET) film to form a 160 μm thick monomer composition film (moisture content of 30%). A comma coater was used for coating, and an applicator roll moved at 0.5 m/min.

Then, polymerization was performed by irradiating UV light of 370 mJ/cm² to the monomer composition film to form a hydrogel polymer film. Herein, a polymerization reaction was performed while drawing the monomer composition film by applying a tension of 60 N/m in the MD direction.

Subsequently, the prepared hydrogel polymer was dried at a temperature of 90° C. for 10 minutes to prepare a super absorbent polymer film (SAP film) having a moisture content of 10 wt % and a thickness of 153 μm.

<Preparation of Absorbent Article>

Comparative Example 1

(1) Preparation of Liquid Impermeable Back Sheet

After polypropylene was spun at a high temperature to form a web on which polypropylene fibers are laminated, the web was bonded through a calendar roll having embossed projections with a predetermined pattern, thereby preparing a liquid impermeable back sheet (nonwoven fabric, pore size: about 40 to 60 μm, basis weight: 12 g/m²) having an embossed surface with a predetermined pattern.

(2) Preparation of Breathable Waterproof Film 50 to 55 wt % of polyethylene, 40 to 45 wt % of calcium carbonate, 1 to 1.5 wt % of a dispersant, 1 to 1.5 wt % of an antioxidant, and 2 to 3 wt % of a colorant were mixed to obtain a waterproof film-forming composition.

The waterproof film-forming composition was fed to an extruder through a feed hopper, and melted. After the molten composition was kneaded in an extruder, it is extruded into a film through a T-die, and cooled. Then, the film was heated to a drawable temperature to draw the film so that the draw ratio was 2.5 to 3.5 times in the mechanical direction. After cooling slowly, it was cut to a certain width and length to obtain a breathable waterproof film (air permeability: 4400 g/m²·24 hr) having a basis weight of 17 g/m².

(3) Preparation of Absorbent Material

A deodorizing composition was prepared by mixing 8 wt % of salicylic acid, 61 wt % of polyethylene glycol, and 31 wt % of cetyl alcohol. Thereafter, the deodorizing composition was coated on a surface of a breathable bonded nonwoven sheet made of cotton spunlace having a basis weight of 30 g/m² using a gravure coating equipment.

Thereafter, the breathable bonded nonwoven sheet coated with the deodorizing composition passed through a hot air drying chamber to evaporate moisture to prepare a core wrap sheet surface-treated with the deodorizing composition.

40 wt % of fluff pulp having a basis weight of 50 g/m$^2$ was mixed with 60 wt % of a polyacrylate-based super absorbent polymer powder having a particle diameter of 250 to 600 μm (average particle diameter: 400 μm, CRC: 34 g/g, 0.3 psi AUP: 28 g/g), and then the mixture was wrapped with the prepared core wrap sheet to prepare an absorbent material having a thickness of 3.0 mm.

(4) Preparation of Liquid Permeable Top Sheet

A spunbond nonwoven fabric having a basis weight of 15 g/m$^2$ and a thickness of 0.1 mm was used as the liquid permeable top sheet. The liquid permeable top sheet was manufactured in a shape that could completely cover a body-side surface of the upper absorbent material so that a liquid such as urine was completely diffused into the upper absorbent material.

(5) Preparation of Absorbent Article

The breathable waterproof film was laminated on one side of the prepared liquid impermeable back sheet. Then, the absorbent material and the liquid permeable top sheet were sequentially laminated on the breathable waterproof film, and adhered to prepare an absorbent article (disposable diaper).

Example 2-1

An absorbent article was prepared in the same manner as in Comparative Example 1, except that the super absorbent polymer film prepared in Example 1-1 was further laminated between the liquid impermeable back sheet and the breathable waterproof film.

Example 2-2

An absorbent article was prepared in the same manner as in Comparative Example 1, except that the super absorbent polymer film prepared in Example 1-2 was further laminated between the liquid impermeable back sheet and the breathable waterproof film.

Example 2-3

An absorbent article was prepared in the same manner as in Comparative Example 1, except that the super absorbent polymer film prepared in Example 1-3 was further laminated between the liquid impermeable back sheet and the breathable waterproof film.

Example 2-4

An absorbent article was prepared in the same manner as in Comparative Example 1, except that the super absorbent polymer film prepared in Example 1-4 was further laminated between the breathable waterproof film and the absorbent material.

Example 2-5

An absorbent article was prepared in the same manner as in Comparative Example 1, except that the super absorbent polymer film prepared in Example 1-1 was further laminated between the breathable waterproof film and the absorbent material.

Example 2-6

An absorbent article was prepared in the same manner as in Comparative Example 1, except that the super absorbent polymer film prepared in Example 1-2 was further laminated between the breathable waterproof film and the absorbent material.

Example 2-7

An absorbent article was prepared in the same manner as in Comparative Example 1, except that the super absorbent polymer film prepared in Example 1-3 was further laminated between the breathable waterproof film and the absorbent material.

Comparative Example 2

An absorbent article was prepared in the same manner as in Example 2, except that a 52 μm-thick super absorbent fiber (SAP fiber, Luquafleece® SAF-52, manufactured by Basf) was laminated between the liquid impermeable back sheet and the breathable waterproof film instead of the super absorbent polymer film.

Comparative Example 3

An absorbent article was prepared in the same manner as in Example 2, except that a 112 μm-thick super absorbent fiber (SAP fiber, Luquafleece® SAF-112, manufactured by Basf) was laminated between the liquid impermeable back sheet and the breathable waterproof film instead of the super absorbent polymer film.

Comparative Example 4

An absorbent article was prepared in the same manner as in Example 2, except that a 1.0 mm-thick absorbent material (40 wt % of fluff pulp, 60 wt % of super absorbent polymer) was laminated between the liquid impermeable back sheet and the breathable waterproof film instead of the super absorbent polymer film.

Experimental Example 1: Evaluation of Physical Properties of Super Absorbent Polymer Film (1) Moisture Absorption The super absorbent polymer film was cut to a size of 15 cm×24 cm, and an aluminum tape was attached to one side of the super absorbent polymer film to prevent moisture, thereby preparing a specimen for analysis of moisture absorption performance. Using the specimen, the moisture absorption of the super absorbent polymer was measured by the following method according to KS F 2611:2019 standard.

1) Maintain the inside of a thermo-hygrostat at 25° C. and 50% relative humidity, cure for 12 hours, and then measure the initial mass (W1).
2) Maintain the inside of the thermo-hygrostat at 25° C. and 75% relative humidity, absorb moisture for 12 hours, and then measure the mass (W2).
3) Calculate the moisture absorption according to the following formula.

$$\text{Moisture absorption } (g/m^2) = (W2 - W1)/0.036$$

(2) Tensile Strength

A specimen was prepared by cutting the super absorbent polymer film in a rectangular shape of 20 mm×60 mm such that cut surface is smooth. Then, an initial grip separation of a tensile strength measuring device (TAXTplus, manufactured by Stable Micro Systems) was set to 20 mm, and the specimen was mounted. The specimen was pulled at a rate of 0.5 mm per second to measure the force (N) at fracture, and the tensile strength (MPa) was obtained by dividing the value by the cross-sectional area (mm²) of the specimen.

Experimental Example 2: Evaluation of Physical Properties of Absorbent Article (1) Evaluation of External Dampness In a chamber with a humidity of 50% and a temperature of 38.7° C., the absorbent article prepared in one of Examples and Comparative Examples was placed on a glass (3) Air Permeability A specimen for measuring air permeability was prepared by thermally bonding a super absorbent polymer film, SAP fiber, or an absorbent material to one side of a breathable waterproof film (basic weight: 17 g/m², air permeability: 4400 g/m²·24 hr, thickness: 25 μm) at 130° C. and 20 kgf/cm, wherein the super absorbent polymer film was applied between the liquid impermeable back sheet and the breathable waterproof film or between the breathable waterproof film and the absorbent material in one of Examples and Comparative Examples.

A specimen having a size of 150 mm (MD)×150 mm (CD) was collected, and the air permeability was measured with a Frazir type air permeability tester according to JIS L 1096. An average value of n=5 was taken as the measured value.

TABLE 1

| | SAP film | SAP film thickness (μm) | SAP film moisture absorption (g/m²) | SAP film tensile strength (MPa) | External dampness | Water vapor barrier permeability (g/m² · 12 hrs) | Air permeability (g/m² · 24 hrs) |
|---|---|---|---|---|---|---|---|
| Comp. Ex. 1 | (Not included) | | — | | ○ | 48 | 4400 |
| Ex. 2-1 | Ex. 1-1 | 17 | 13.9 | 9.9 | X | 36 | 4200 |
| Ex. 2-2 | Ex. 1-2 | 45 | 25.7 | 23.8 | X | 32 | 4000 |
| Ex. 2-3 | Ex. 1-3 | 149 | 77.3 | 25.8 | X | 29 | 3200 |
| Ex. 2-4 | Ex. 1-4 | 153 | 81.7 | 22.0 | X | 38 | 3900 |
| Ex. 2-5 | Ex. 1-1 | 17 | 13.9 | 9.9 | X | 37 | 4200 |
| Ex. 2-6 | Ex. 1-2 | 45 | 25.7 | 23.8 | X | 33 | 4000 |
| Ex. 2-7 | Ex. 1-3 | 149 | 77.3 | 25.8 | X | 29 | 3200 |
| Comp. Ex. 2 | (SAP fiber, 52 μm) | | — | | ○ | 45 | 4200 |
| Comp. Ex. 3 | (SAP fiber, 112 μm) | | — | | ○ | 46 | 4100 |
| Comp. Ex. 4 | (Absorbent material, 1 mm) | | — | | X | 5 | 1220 | plate, and 350 ml of physiological saline (0.9% NaCl aqueous solution) at 37° C. was injected into the liquid permeable top sheet of the absorbent article.

After 30 minutes, it was checked whether or not vapor was condensed on the glass plate. When vapor was condensed, it was evaluated as having external dampness (O), and when no vapor was condensed, it was evaluated as no external dampness (X).

(2) Water Vapor Barrier Permeability 1000 ml of distilled water was injected into the absorbent article having an area of 25 cm*10 cm prepared in one of Examples and Comparative Examples for absorption. Thereafter, the absorbent article absorbing the distilled water was placed in a thermo-hygrostat (humidity: 50%, temperature: 38.7° C.) for 12 hours. Then, the water vapor barrier permeability (g/m²·12 hr) expressed as an increase in weight per area of the absorbent article was calculated by the following formula.

$$\text{Water vapor barrier permeability (g/m}^2\text{·12 hr)} = (W2 - W1)/T$$

(In the formula,

W1 is the weight per area (g/m²) of the absorbent article absorbing distilled water before constant temperature and humidity treatment, W2 is the weight per area (g/m²) of the absorbent article after constant temperature and humidity treatment, and T is the time taken for constant temperature and humidity treatment, which is 12 hr.)

As a result of the experiment, Examples 1-1 to 1-4 were confirmed to exhibit excellent moisture absorption and tensile strength. In addition, the absorbent articles of Examples 2-1 to 2-7 were confirmed to have significantly improved external dampness compared to Comparative Example 1 due to the super absorbent polymer film interposed between the liquid impermeable back sheet and the breathable waterproof film or between the breathable waterproof film and the absorbent material without lowering air permeability.

In addition, as a result of performing a simulated wearing test (inject saline at 37° C. into the liquid permeable top sheet of the diaper, leave it at 36.5° C. for 5 minutes, and check the feel of the back sheet) to evaluate usability of diapers in actual use, the diapers of Examples 2-1 to 2-7 exhibited a warmer and drier feel than the diapers of Comparative Example 1.

However, when the super absorbent fiber was used instead of the super absorbent polymer film, the air permeability was maintained excellently, but the moisture permeability was poor, so the effect of improving external dampness could not be secured. In addition, when the absorbent material was applied instead of the super absorbent polymer film, it was confirmed that the external dampness was improved, but the air permeability was greatly reduced.

DESCRIPTION OF SYMBOLS 1, 2, 3, 4: Absorbent articles
11: Liquid impermeable back sheet

12: Breathable waterproof film
13: Absorbent material
14: Liquid permeable top sheet
20: Super absorbent polymer film

The invention claimed is:

1. A super absorbent polymer film, which is a single layer, and has a thickness of 10 TO 200 μm and a moisture absorption of 10 to 100 $g/m^2$ measured according to KS F 2611 standard, wherein the super absorbent polymer film is prepared by a preparation method including the steps of: preparing a monomer composition by mixing an acrylic acid-based monomer having at least partially neutralized acidic groups, a cellulose-based thickener, a moisturizing agent, an internal cross-linking agent, a polymerization initiator, and a solvent; casting the monomer composition on a substrate; polymerizing the monomer composition by irradiating heat and/or light to form a hydrogel polymer, wherein drawing is performed during the polymerizing; and drying the hydrogel polymer film.

2. The super absorbent polymer film of claim 1, which has a moisture content of 1 to 15% and a tensile strength of 5 to 50 MPa.

3. An absorbent article comprising a liquid impermeable back sheet; a breathable waterproof film; an absorbent material containing a super absorbent polymer powder and pulp; and a liquid permeable top sheet, wherein the super absorbent polymer film of claim 1 is included between the liquid impermeable back sheet and the breathable waterproof film and/or between the breathable waterproof film and the absorbent material.

4. The absorbent article of claim 3, wherein the super absorbent polymer film is laminated on one side of the liquid impermeable back sheet; and/or on one side or both sides of the breathable waterproof film.

5. The absorbent article of claim 3, wherein the super absorbent polymer film is laminated on one side of the breathable waterproof film, and air permeability of the laminated super absorbent polymer film and breathable waterproof film is 3000 to 5000 $g/m^2 \cdot 24$ hr.

6. The absorbent article of claim 3, wherein the liquid impermeable back sheet is a nonwoven fabric having a pore size of 20 to 1000 μm.

7. The absorbent article of claim 3, wherein the breathable waterproof film has air permeability of 2000 to 5000 $g/m^2 \cdot 24$ hr.

8. The absorbent article of claim 3, wherein the absorbent material contains 10 to 90 wt % of the super absorbent polymer powder.

9. The absorbent article of claim 3, wherein the liquid permeable top sheet has a basis weight of 15 to 30 $g/m^2$.

* * * * *